(12) United States Patent
Fuller

(10) Patent No.: US 9,412,481 B1
(45) Date of Patent: Aug. 9, 2016

(54) METHOD AND DEVICE FOR PRODUCING AND USING LOCALIZED PERIODIC INTENSITY-MODULATED PATTERNS WITH X-RADIATION AND OTHER WAVELENGTHS

(71) Applicant: Michael Keith Fuller, Salinas, CA (US)

(72) Inventor: Michael Keith Fuller, Salinas, CA (US)

(*) Notice: Subject to any disclaimer, the term of this patent is extended or adjusted under 35 U.S.C. 154(b) by 76 days.

(21) Appl. No.: 13/999,172

(22) Filed: Jan. 22, 2014

Related U.S. Application Data

(60) Provisional application No. 61/849,258, filed on Jan. 22, 2013.

(51) Int. Cl.
| | |
|---|---|
| *G21K 1/10* | (2006.01) |
| *G01N 23/20* | (2006.01) |
| *G01N 23/201* | (2006.01) |
| *G01N 23/04* | (2006.01) |

(52) U.S. Cl.
CPC *G21K 1/10* (2013.01); *G01N 23/04* (2013.01); *G01N 23/201* (2013.01)

(58) Field of Classification Search
CPC . G01N 23/04; G01N 23/20; G01N 23/20008; G01N 23/20075; G01N 23/20083; G01N 23/201; G21K 1/06; G21K 1/065; G21K 1/10; A61B 6/484
USPC .......................................... 378/62, 70, 86–89
See application file for complete search history.

(56) References Cited

U.S. PATENT DOCUMENTS

| 5,802,137 A | * | 9/1998 | Wilkins | A61B 6/484 |
| | | | | 250/363.1 |
| 2009/0060134 A1 | * | 3/2009 | Fuller | 378/85 |
| 2015/0055744 A1 | * | 2/2015 | Anton | G21K 1/065 |
| | | | | 378/36 |

FOREIGN PATENT DOCUMENTS

WO     WO 2011011014 A1 * 1/2011

OTHER PUBLICATIONS

"An X-ray Bilens Nanointerferometer", http://www.esrf.eu/news/spotlight/spotlight90, Aug. 19, 2009.*
Liping et al, "Non-Diffraction Fringes Produced by Thin Biprism", Optica Applicata, vol. XLII, No. 4, 2012.*
"An X-ray Bilens Nanointerferometer", http://www.ersf.eu/spotlight/spotlight90 Aug. 19, 2009.*
Shabel'nikov et al, "Refractive X-Ray Optics: Step From Focusing to Interferometric Devices", Design and Microfabrication of Novel X-Ray Optics, Proceedings of SPIE, vol. 4783 (2002), p. 55-64.*

* cited by examiner

*Primary Examiner* — Robert Kim
*Assistant Examiner* — David E Smith

(57) ABSTRACT

A method and device is disclosed for the generation of high-contrast, localized sinusoidal patterns or stepped-intensity modulated patterns from spatially non-coherent or coherent illumination, and using such patterns for imaging the internal features of objects.

13 Claims, 7 Drawing Sheets

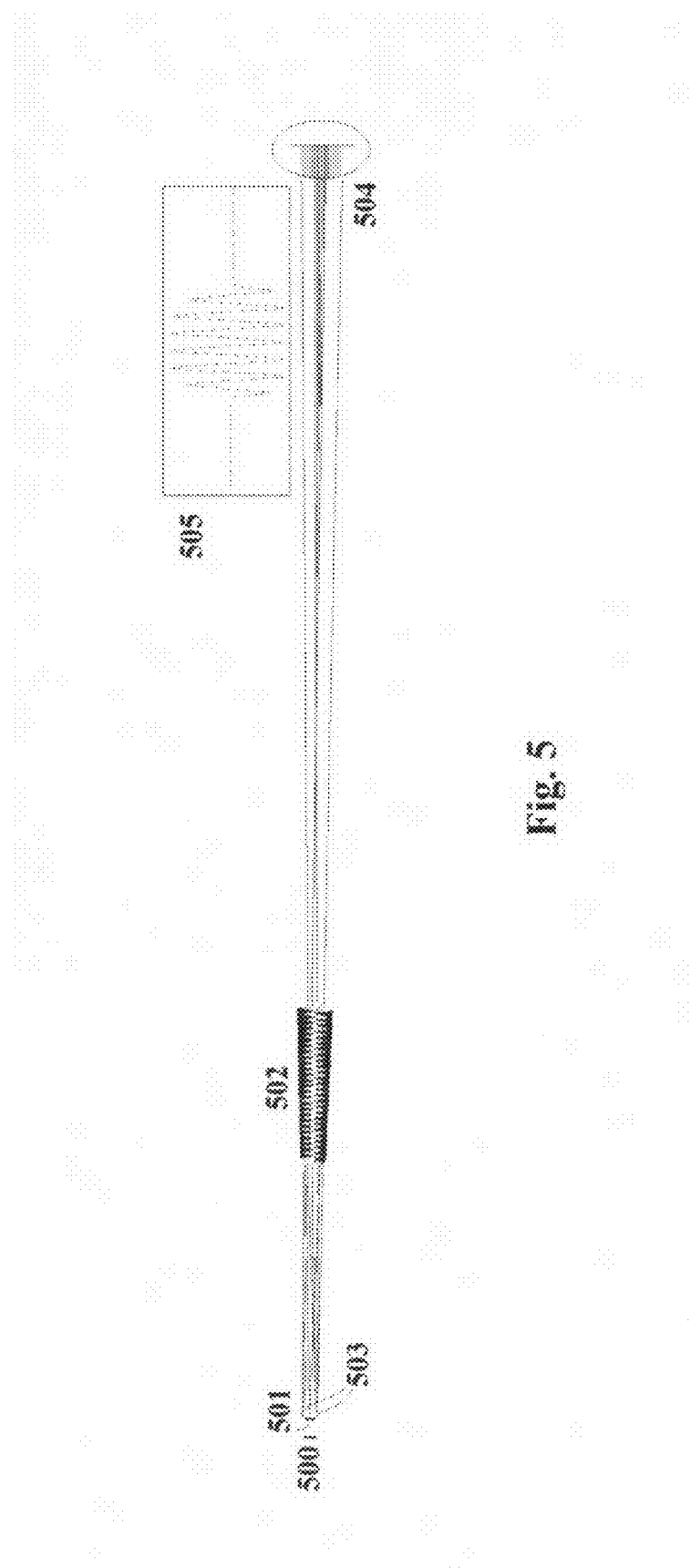

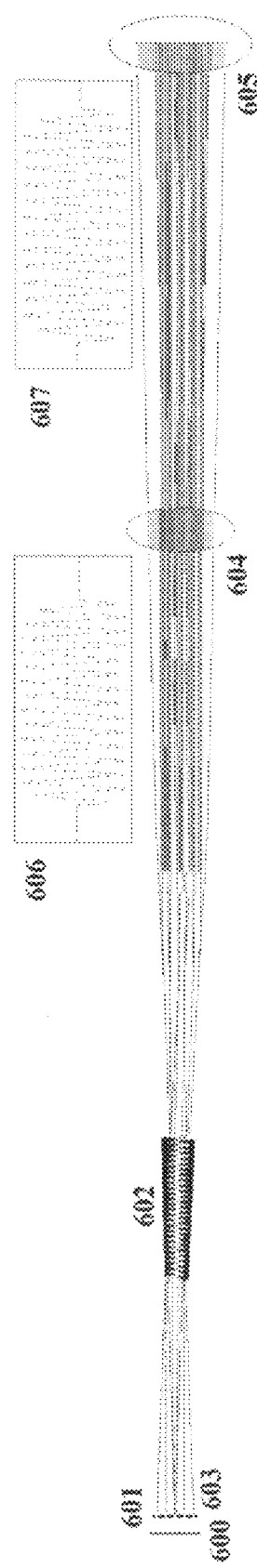

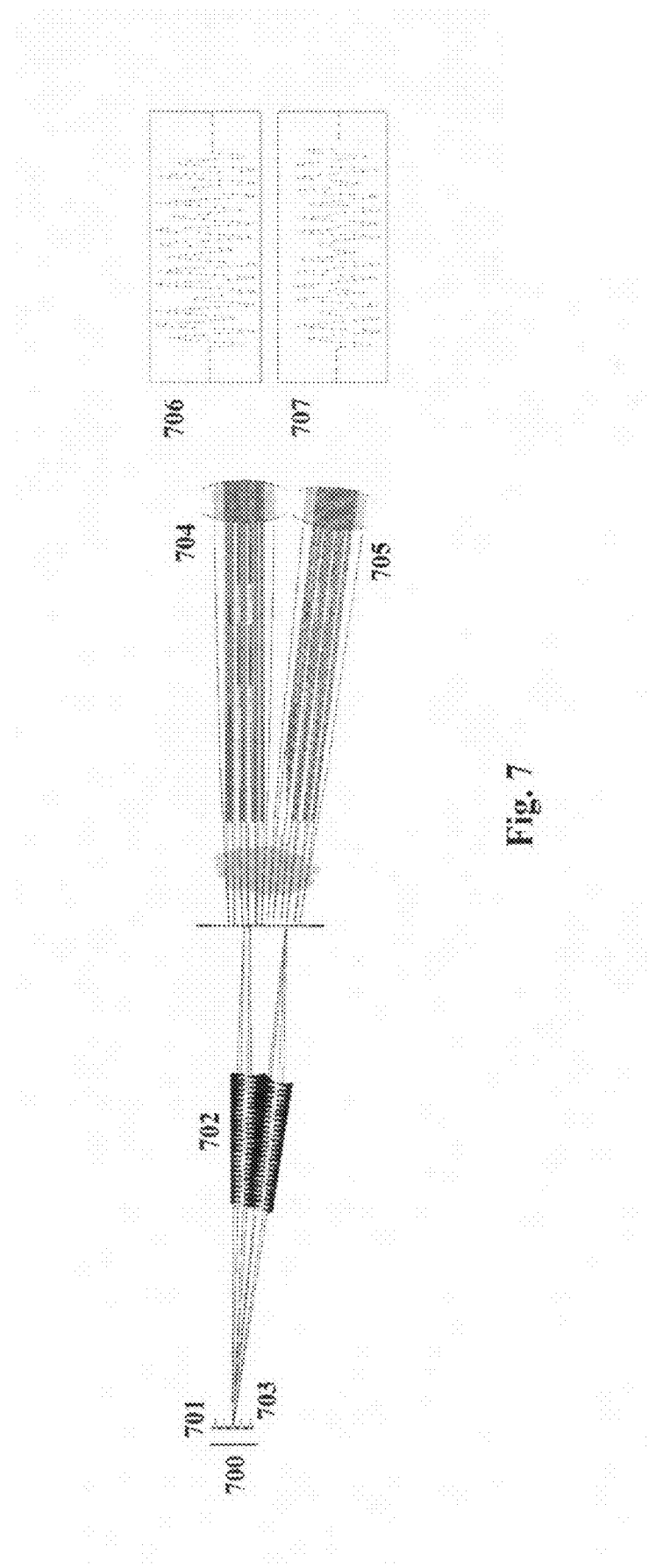

METHOD AND DEVICE FOR PRODUCING AND USING LOCALIZED PERIODIC INTENSITY-MODULATED PATTERNS WITH X-RADIATION AND OTHER WAVELENGTHS

A method and device is disclosed for the generation of high-contrast, localized sinusoidal patterns or stepped-intensity modulated patterns from spatially non-coherent or coherent illumination, and using such patterns for imaging the internal features of objects.

FIELD

The present invention relates to the generation of high-contrast, localized sinusoidal patterns or stepped-intensity modulated patterns from spatially non-coherent illumination, in particular hard x-rays, useful for obtaining images using phase-shifted and scattered x-rays and measuring wavefront shapes.

BACKGROUND

Compared to traditional x-ray absorption radiography, phase radiography is better suited for visualizing soft-tissue structures which do not appreciably absorb x-rays, but which may contain non-absorptive structural details. Internal structures may produce a measurable deviation in the direction and velocity of the incident radiation because of local variations in the refractive index, and variations in density and thickness of those structures. Phase disturbances occur at interfaces between soft-tissue planes that have slightly different refractive indices and thicknesses. Within soft-tissues, incident radiation is refracted by spatially oriented molecular and atomic planes, thereby experiencing a significant shift in phase, corresponding to a change in direction.

For hard x-rays, the cross section for absorption, which generates the contrast in conventional radiography, is usually much smaller than that for elastic scattering. The elastic scattering causes a phase shift of the wave passing through matter. Thus, the possibility to record the elastic scattering and phase shift of x-rays opens the potential for greatly enhanced contrast and, in consequence, reduction of the applied x-ray dose. Reduction of the dose is desirable i) because of health risks for patients exposed to x-rays, and ii) because of the reduced exposure times.

Several methods to detect phase variations in the radiation behind the sample were developed in the past years. They can be classified into interferometric methods, techniques using an analyzer crystal, and free-space propagation methods. These methods differ in the nature of the signal recorded, the experimental setup, and the requirements on the illuminating radiation (especially its spatial coherence and monochromaticity). Many experimental results known in the prior art were obtained at synchrotron x-ray sources, which are highly expensive installations and are only available at distinct scientific facilities. The commercial impact of an invention in context with radiography will greatly depend on whether an x-ray tube is suitable as radiation source or whether the method is restricted to use at synchrotron radiation facilities because of the required degree of coherence.

The use of gratings as optical elements in hard x-ray phase imaging has shown the potential of overcoming the problems that so far impair the wider use of phase contrast in x-radiography and tomography. Several different geometries of grating-based interferometers for hard x-rays have been investigated recently.

The Talbot-Lau self-imaging effect, i.e., its replication in the longitudinal direction without the use of a lens, has been widely studied and used for a number of applications, including x-ray phase imaging and x-ray dark-field scatter imaging. Talbot self-imaging can be described in the following way: a (quasi-)monochromatic wavefield of wavelength $\lambda$ with lateral period $1/v_1$ is also longitudinally periodic. The longitudinal period $z_T$—often referred to as the Talbot-distance—is given as $z_T = 2/\lambda v_1^2$. A common practical implementation of the Talbot effect is achieved when one 1D grating is illuminated by x-rays proceeding from a monochromatic spatially coherent point source and the grating pattern is replicated at certain far-field distances.

The Lau effect is the spatially incoherent counterpart of the Talbot effect. The Lau effect is obtained when one allows the superposition in consonance of Talbot fringes generated by a series of mutually incoherent quasi-monochromatic sources. A common practical implementation of the Lau effect is achieved when two 1D gratings, oriented parallel to each other, are illuminated by the x-rays proceeding from a quasi-monochromatic spatially incoherent planar source, and the grating pattern is replicated at certain far-field distances.

The second grating divides the incoming beam essentially into the two first diffraction orders. The angle between the two diffracted beams is so small that they overlap almost completely. In the overlap region downstream of the second grating, the diffracted beams interfere and form linear periodic fringe patterns in planes perpendicular to the optical axis, at a Talbot distance down-stream of the second grating.

The period of the x-ray interference pattern is usually in the range of a few microns, which can only be conveniently resolved by a very high resolution detector in combination with a very intense illumination and hence, limits the field-of-view significantly. For this reason, an analyzer grating, typically an absorption grating, is placed at a fractional Talbot length to analyze the interference pattern. The analyzer grating, normally having the same period as the self-imaged interference fringes, can be scanned in the transverse direction in a technique called "phase-stepping." An alternative approach is the retrieval of the differential phase by using Moiré fringes when inclining the analyzer grating against the source gratings. Large-format x-ray gratings with high aspect ratios and small periods are difficult to fabricate and do not efficiently use x-rays from laboratory sources.

A publication (PCT WO 2011/011014 A1), discloses a scattering imaging method using an intensity modulating grid, which is easier to fabricate than a diffractive grating. A detector captures a raw image of the modulated intensity pattern. A comparative Fourier Transform analysis method is used to obtain both a scattering image and a phase-contrast image from the detected modulated intensity pattern. The disclosed comparative Fourier Transform analysis method of PCT WO 2011/011014 A1 is hereby reference in full. However, the overall described method (PCT WO 2011/011014 A1) does not allow for slight shifts in phase and ultra small angle scattering as the simple shadowgraph image acquisition method is limited in the grid-pitch and grid-to-detector distance. Also, the method (PCT WO 2011/011014 A1) requires sample movement and/or intensity variation during exposure to remove analytical confusion from sharp-edge absorptive features in certain samples. Thus, the problems of the method (PCT WO 2011/011014 A1) make it unsuitable for phase and scattering imaging of many low density objects.

A technique, published by Doblas, et al, "Axial resonance of periodic patterns by using a Fresnel biprism" (J. Opt. Soc. Am. A/Vol. 30, No. 1/January 2013) formalizes the production of resonant fringes with a visible-light Fresnel biprism.

That research, hereby reference in full, considered some possible alternatives, (such as the Wollaston prism, Lloyd's mirror and the Kösters prism) to the Fresnel biprism. That research did not discuss a Billet split lens, and did not discuss the use of x-radiation.

An alternative method in needed to produce high-contrast localized sinusoidal or stepped-intensity modulated patterns with spatially non-coherent illumination. A need also exist for an alternative method that would allow progressively increasing periods to allow for easier detection and analysis. Lastly, a need exist for a more efficient use of the radiation from a laboratory x-ray tube source.

SUMMARY OF THE INVENTION

It is the object of the present invention to provide a method and apparatus for modulated patterns from spatially non-coherent illumination, in particular hard X-rays, useful for obtaining images using phase-shifted and scattered X-rays, which does not rely on synchrotron x-ray sources.

This objective is achieved in the present invention by a device for obtaining phase contrast x-ray images and x-ray scattering images, comprising:
a) an x-ray source, preferably a standard polychromatic X-ray source,
b) an x-ray optical element, preferably in transmission geometry, that acts to separate and focus x-ray beams, and
c) a position-sensitive detector with spatially modulated detection sensitivity. This modulation acts as an analyzer for the intensity pattern formed by the optical separator; it can be integrated in the detector or separate from it.

This device unifies all the requested requirements in using only a conventional X-ray source instead of a synchrotron source and in using only two optical elements, one for separating the x-rays having passed through a sample to be investigated, and the other one for delivering the spatially modulated detection sensitivity.

In a preferred embodiment of the present invention the optical separator is a compound refractive x-ray lens, useful for collecting and focusing x-rays from a small origin onto a detector surface.

In another embodiment of the present invention the optical separator is a Billet split lens, that is, a compound refractive x-ray lens, but split into two halves, with a small displacement between the two halves.

In another embodiment of the present invention the optical separator is a Fresnel bi-prism, that is, a compound refractive x-ray prism.

Further, the modulation of the detector sensitivity can be achieved by a one- or two-dimensional grating structure with high X-ray absorption contrast, placed immediately in front of the detector. This analyzer grating may serve as an anti-scatter grid, or an anti-scatter grid can be used as the analyzer grating.

Furthermore, the refractive properties of the optical elements and the distance between the elements and detector can be adapted to a photon energy corresponding to an emission line of the X-ray generator used as the source.

In the configurations described in the previous paragraphs, the flux can be increased and data acquisition time thus reduced, by using, instead of a single line or spot source, a one- or two-dimensional array of individual physical or virtual sources that may be mutually incoherent. This array of sources may be generated by an aperture mask with line- or dot-shaped openings. Alternately, the array of sources is generated by electron optics that creates an array of electron line or dot foci on the anode of the X-ray source. This can be achieved i.e. by generating the array of sources using electron optics that either scans a single line or dot focus across the anode surface of the X-ray source or projects an array of lines or dots onto the anode surface. Alternately or additionally, the array of sources can be generated by using an X-ray source comprising an anode which is structured either topographically or has assembled in a mosaic manner from different materials.

Again in order to improve the scanning properties of the device, means for rotating the sample relatively to the remaining components can be comprised in order to perform data collection for a tomography scan.

The device is consistent with an analysis procedure implemented for phase-stepping scan data that comprises the steps of fitting for each element of the detector the intensity curve measured in the element to an intensity curve modeled or measured separately without the beam distortions under study, where at least one of the fit parameters is the shift of the curve along the position axis of the scan.

The device is consistent with the scanning techniques carried out by implementing an analysis procedure for phase-stepping scan data that comprises the steps of calculating for each element of the detector the Fourier transform or at least one Fourier component of the intensity curve measured in the element, and then retaining the phase of one or more Fourier components as a signal for further processing.

The device is consistent with an analysis procedure implemented for scattering imaging that comprises the steps of converting the raw image into a spatial frequency domain image. In the spatial frequency domain image, various peaks are visible, which corresponds to integer multiples of the basic spatial frequencies of the dark regions of the modulated intensity pattern projected on the detector surface. An Nth-order peak is selected from the image in the spatial frequency domain. A spatial frequency domain filter is applied to an area around the Nth-order peak. An inverse transform is performed to obtain an Nth-order harmonic image in the space domain using the area around the Nth order peak. Calibration is performed on the Nth-order harmonic image by dividing that image with an Nth-order harmonic image of a reference image that was taken without a sample. The calibration can include taking a ratio of corresponding portions of the Nth-order harmonic image and the reference image. A Kth-order harmonic is selected from the image in the spatial frequency domain and an area around it is multiplied with a filter and is inverse transformed in order to obtain a Kth-order harmonic image in the space domain. Calibration is performed on the Kth-order harmonic image in the space domain using the same calibration technique described above. The intensity ratio between a Kth-order harmonic image and an Nth-order harmonic image provides an image of X-ray scattering distribution. The phase of a Kth-order harmonic image represents gradients of the index of refraction in the direction perpendicular to the grid lines. The grid can have different patterns of opaque and transparent regions, such as, linear, rectangular or hexagonal patterns. Other patterns can also be used whose Fourier transformation contains multiple peaks that are arranged at different angles around the origin.

BRIEF DESCRIPTION OF THE SEVERAL VIEWS OF THE DRAWINGS

FIG. 5 is a schematic diagram of an x-ray Fresnel bi-prism, provided here for descriptive clarity.

FIG. 6 is a schematic diagram of an apparatus according to one embodiment of the disclosed invention, for generating a modulated intensity pattern(s) which may include a high-frequency component using an x-ray Fresnel bi-prism arrangement.

FIG. 7 is a schematic diagram of an apparatus according to one embodiment of the disclosed invention, for generating a multiple modulated intensity patterns which may be used for examining large samples using x-ray Fresnel bi-prisms.

DETAILED DESCRIPTION OF THE INVENTION

The present invention overcomes the drawbacks of the prior art by allowing scattering and phase-contrast images to be obtained using commercially available grids, focusing optics and x-ray sources.

In one embodiment, a method uses an intensity grid to modulate the intensity of a beam of an X-radiation illumination beam and, in a first-step, an image of the modulated intensity source pattern is captured by one (or an array of) focusing X-ray optic(s) and brought to focus at a detector. A record is kept of the first-step image, which is used as a reference image for analysis purposes. A similar image is captured in a second-step by placement of a sample between the focusing optics and the detector. The method works for large distances between the optics/sample and the detector. An analytical comparison is performed on the sample image as related to the reference image.

In another embodiment, a method allows the observation of interference fringes using extended sources, that is a light-wave is separated to two beams and brought back together again at a detector. Interference results as long as the original coherence between the two beams had not been destroyed.

A spherical wavefront proceeding from a point source illuminates a Billet split lens with a focal length f and a separation h, the exiting wavefront becomes split into two spherical waves that proceed from two real point sources placed at the image plane i and separated by the distance a=h(i/o). Similarly, a spherical wavefront proceeding from a point source at a distance o illuminates a Fresnel biprism, the exiting wavefront becomes split into two spherical waves that virtually proceed from two virtual point sources placed a the plane of the source and separated by the distance $a=(n-1)o(\alpha_1+\alpha_2)$ where n is the refracting index and $\alpha_1$ and $\alpha_2$ are the refringence angles of the prisms. In both cases, the secondary point sources, virtual or real, are mutually coherent. Thus, both cases produce an interference pattern in the region of the geometrical superposition of rays coming from the secondary sources.

A quasi-monochromatic source, composed by an array of mutually incoherent, equidistant point sources arranged perpendicular to the optic's edge, also produces fringes, but with discreet planes of maximum visibility along the axis of propagation. These planes are not equidistant, however, the position of such planes does not depend on the number of point sources. The greater the number of point sources, the higher the axial localization of the planes of high visibility. Slit sources are an alternative to point sources in this invention.

The foregoing and other objects, features, and advantages of the invention will become more apparent from the following detailed description, which proceeds with reference to the accompanying figures.

General Aspects

Figure 1:
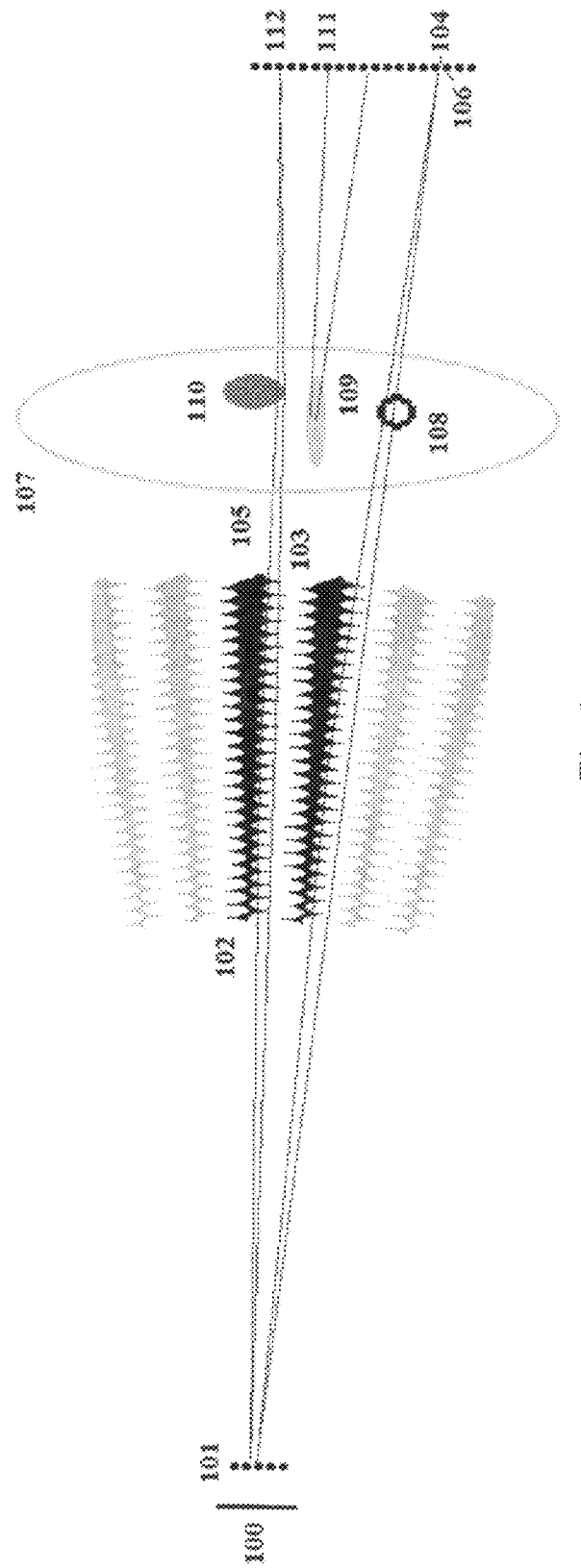
FIG. 1 is a schematic diagram of an apparatus according to one embodiment of the disclosed invention, for generating a modulated intensity pattern(s) which may include a higher-frequency component(s) and a lower-frequency component (s).

FIG. 1, is a schematic diagram according to one embodiment of the disclosed invention, shown in the "sample-present" case, having an x-ray source 100, a primary periodic x-ray grid 101 for modulating transmitted intensity, and in the same orientation of the grid, an array of focusing optics 102, such as an array of compound refractive x-ray lenses. Portions of the primary grid-modulated field of x-radiation 103 are captured and focused by each individual optic in the array such that a pattern is formed of fixed-period bright stripes of high intensity 104 interlaced with dark stripes of near-zero intensity. Such pattern of a 1-D grid imaged with 1-D optics are inverted, while patterns of 2-D grids imaged with 2-D optics are reversed and inverted. Patterns can be magnified images of grids or de-magnified images of grids, but are localized to the image plane. With no sample present, such pattern can be recorded as a reference image. With a sample 107 placed in the x-radiation beam paths 105, near to the array of focusing optics 102, a modified pattern can be recorded. Such sample 107 may include internal features of different types as related to their primary interaction with x-rays, such as absorptive and/or inelastic scattering features 108, elastic scattering features 109, and/or refractive features 110. Absorptive/inelastic features 108 are observed as reduced intensity from the reference image, within the reference image locations of bright stripes. Elastic scattering features 109, are observed as increased intensity from the reference image, within the reference image locations of near-zero intensity 111. Refractive features 110 are observed as variations in the locations of the boundary edges of bright stripes 112, as different from their reference image locations. Comparison of the modified pattern, recorded with sample, to the reference pattern, recorded without sample, can reveal these features.

Figure 2:
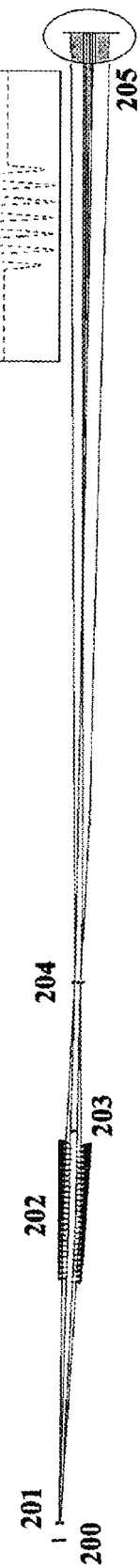
FIG. 2 is a schematic diagram of an x-ray Billet split-lens arrangement, provided here for descriptive clarity.

FIG. 2, is a schematic diagram of a common technique known as a Billet split-lens arrangement, provided here for descriptive clarity, having an x-ray source 200, an x-ray pinhole or slit aperture 201, and a split focusing optic 202, such as a split compound refractive x-ray lens. The aperture 201 reduces the effective source size to coherence conditions, as required by the arrangement of a particular setup. A beam block 203 stops x-rays from transmitting between the split lens. X-rays from the aperture 201 are captured by each half of the split lens and focused to two real secondary origins of x-rays 204, where the distance between the two secondary sources 204 is less than the coherence length of the distant origin 201. Interference fringes 205 result in the portions of overlapped beams, as the secondary origins 204 are considered mutually coherent, spatially and temporally, as they were produced from the same origin 201. The modulated intensity field 206 progresses longitudinally, that is non-localized in the z axis, from the first intersection of the overlapped beams, with progressive increases in the period of the fringe pattern and without any regions of reduced fringe visibility.

Figure 3:
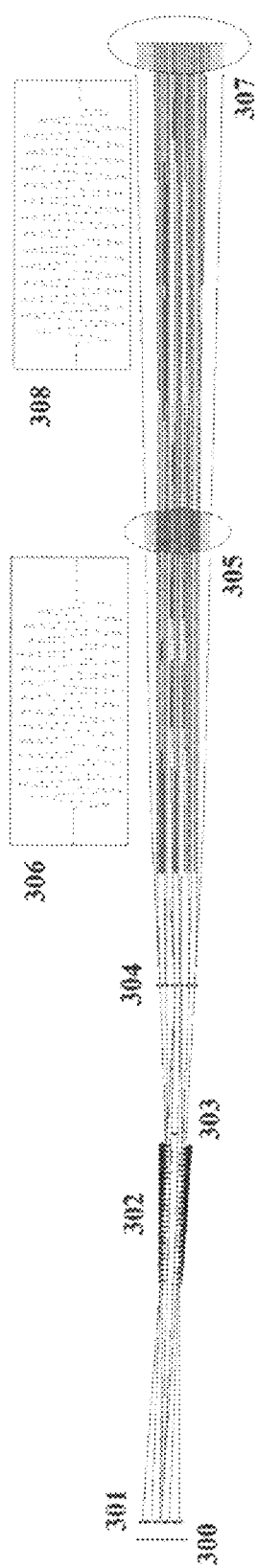
FIG. 3 is a schematic diagram of an apparatus according to one embodiment of the disclosed invention, for generating a modulated intensity pattern(s) which may include a high-frequency component using an x-ray Billet split-lens arrangement.

FIG. 3, is a schematic diagram according to one embodiment of the disclosed invention, showing a modified Billet split-lens arrangement, having an x-ray source 300, an x-ray periodic grating or grid 301, and in the same orientation of the grid, a split focusing optic 302, such as a split compound refractive x-ray lens. The periodic grid 301 produces mutually incoherent sources, as required by the arrangement of a particular setup. A beam block 303 stops x-rays from transmitting between the split lens. X-rays from the grid 301 are captured by each half of the split lens 302 and focused to multiple real secondary origins of x-rays 304. Interference fringes result in the portions of multiple overlapped beams. The modulated intensity field progresses longitudinally from the first intersection of overlapped beams, localized in the z axis, that is highly visible fringes appear only at certain distances in the z-direction, where the laterally displaced fringe patterns superpose resonantly, giving rise to fringe patterns of high visibility. Distances between such successive visible regions 305, 307 are not uniform. Progressive increases in the period of the fringe pattern 306, 308 also advance, even through intermediate regions of reduced fringe visibility.

Figure 4:
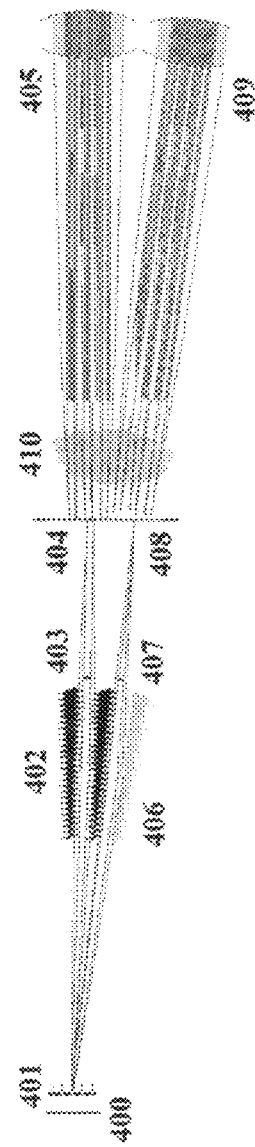
FIG. 4 is a schematic diagram of an apparatus according to one embodiment of the disclosed invention, for generating a multiple modulated intensity patterns which may be used for examining large samples using x-ray Billet split-lenses.

FIG. 4, is a schematic diagram according to one embodiment of the disclosed invention, having an x-ray source 400, an x-ray periodic grating or grid 401, and in the same orientation of the grid, an array of split focusing optics 402, 406 such as a split compound refractive x-ray lenses. The periodic grid 401 produces mutually incoherent sources, as required by the arrangement of a particular setup. Beam blocks 403, 407 stop x-rays from transmitting between the split lenses. X-rays from the grid 401 are captured by each half of each split lens 402, 406 and focused to multiple real secondary origins of x-rays 404, 408. Interference fringes result in the portions of multiple overlapped beams. The modulated intensity field progresses longitudinally from the first intersection of overlapped beams, localized in the z axis, that is highly visible fringes appear only at certain distances in the z-direction 405, 409. The distances between such successive visible regions 405, 409 are not uniform. With no sample present, such fringe patterns can be recorded as reference images. With a sample 410 placed in the x-radiation beam paths, near to the array of focusing optics 402, 406 modified patterns 411, 412 can be recorded. Such sample 410 may include internal features of different types as related to their primary interaction with x-rays, such as absorptive and/or inelastic scattering features, elastic scattering features, and/or refractive features. Absorptive/inelastic features are observed as reduced intensity from the reference image, within the reference image locations of bright stripes. Elastic scattering features, are observed as increased intensity from the reference image, within the reference image locations of near-zero intensity. Refractive features are observed as variations in the locations of the boundary edges of bright fringes, as different from their reference image locations. Comparison of the modified pattern, recorded with sample, to the reference pattern, recorded without sample, can reveal these features.

FIG. 5, is a schematic diagram of a common technique known as a Fresnel bi-prism arrangement, provided here for descriptive clarity, having an x-ray source 500, an x-ray pinhole or slit aperture 501, and at least. The aperture 501 reduces the effective source size to coherence conditions, as required by the arrangement of a particular setup. X-rays from the aperture 501 are captured by each prism and dispersed as from two virtual origins of x-rays 503, where the distance between the two virtual origins 503 is less than the coherence length of the real distant origin 501. Interference fringes 504 result in the portions of overlapped beams, as the secondary origins 503 are considered mutually coherent, spatially and temporally, as they were produced from the same origin 501. The modulated intensity field 505 progresses longitudinally, that is non-localized in the z axis, from the first intersection of the overlapped beams, with progressive increases in the period of the pattern and without any regions of reduced fringe visibility.

FIG. 6, is a schematic diagram according to one embodiment of the disclosed invention, showing a modified Fresnel bi-prism arrangement, having an x-ray source 600, an x-ray periodic grating or grid 601, and in the same orientation of the grid, two separated dispersion optics 602, such as a two compound refractive x-ray prisms. The periodic grid 601 produces mutually incoherent sources, as required by the arrangement of a particular setup. X-rays from the grid 601 are captured by each prism and dispersed as from two virtual origins of x-rays 603. Interference fringes result in the portions of multiple overlapped beams. The modulated intensity field progresses longitudinally from the first intersection of the overlapped beams, localized in the z axis, that is, highly visible fringes appear only at certain distances in the z-direction. The distances between such successive visible regions 604, 605 are not uniform. Progressive increases in the period of the fringe pattern 606, 607 also advance, even through intermediate regions of reduced visibility.

FIG. 7, is a schematic diagram according to one embodiment of the disclosed invention, having an x-ray source 700, an x-ray periodic grating or grid 701, and in the same orientation of the grid, sets of two separated dispersion optics 702, such as a two compound refractive x-ray prisms. The periodic grid 701 produces mutually incoherent sources, as required by the arrangement of a particular setup. X-rays from the grid 701 are captured by each half of each prism and dispersed as from two virtual origins of x-rays 703. Interference fringes result in the portions of multiple overlapped beams. The modulated intensity field progresses longitudinally from the first intersection of the overlapped beams, localized in the z axis, that is highly visible fringes appear only at certain distances in the z-direction 704, 705. With no sample present, such fringe patterns can be recorded as reference images. With a sample placed in the x-radiation beam paths, near to the sets of prism pairs 702, modified patterns 706, 707 can be recorded. Such sample may include internal features of different types as related to their primary interaction with x-rays, such as absorptive and/or inelastic scattering features, elastic scattering features, and/or refractive features. Absorptive/inelastic features are observed as reduced intensity from the reference image, within the reference image locations of bright stripes. Elastic scattering features, are observed as increased intensity from the reference image, within the reference image locations of near-zero intensity. Refractive features are observed as variations in the locations of the boundary edges of bright fringes, as different from their reference image locations. Comparison of the modified pattern, recorded with sample, to the reference pattern, recorded without sample, can reveal these features.

What is claimed is:

1. A system for forming an image of an object, said image including internal features of said object, said system comprising: means for generating penetrating radiation beams; said means for generating having multiple point origins of said beams providing that said beam origins have linear alignment; one or more compound refractive radiation lenses placed between said beam origins and said object; means for supporting said object to provide that said beams are directed through said object and through said one or more compound refractive radiation lenses; said radiation imaging optic arranged to form at least a partial image of said beams origins presented on a detector screen; said partial image including at least one of phase and scattering content of said object's internal features in a direction along the linear alignment axis of said beam origins.

2. The system of claim 1 wherein said one or more compound refractive radiation lenses are one or more one-dimensional cylindrical lenses, arranged to collect and focus said image in one dimensions.

3. The system of claim 1 wherein said one or more compound refractive radiation lenses are one or more two-dimensional spherical lenses, arranged to collect and focus said image in two dimensions.

4. The system of claim 1 wherein said object and said one or more compound refractive radiation lenses are arranged close-coupled to form a compound object/optic for collecting, focusing, and modifying said image of beam origins.

5. A system of image preparation and display, whereby an image obtained according to the system of claim 4 with said object present is prepared by mathematical analysis of said modification of said image of beam origins.

6. A system of a modified Billet split-lens arrangement, having a linear array of small radiation origins, such that the origins are coherent, and a split radiation imaging optic, comprising a split compound refractive x-ray lens, such system forming multiple real secondary origins of radiation and interference fringes resulting in the portions of multiple overlapped radiation beams, wherein such modulated intensity field progresses longitudinally from the first intersection of overlapped beams, localized in the longitudinal axis in regions of highly visible fringes at certain distances where the laterally displaced fringe patterns superpose resonantly.

7. A system for forming an image of an object, said image including internal features of said object, said system comprising the system of claim 6 with an object in said radiation beams: said image including at least one of phase and scattering content of said object's internal features in a direction along the linear alignment axis of said beam origins.

8. The system of claim 7 wherein said object and said radiation imaging optic are arranged close-coupled to form a compound object/optic for transmitting and modifying said radiation beams.

9. A system of image preparation and display, whereby an image obtained according to the system of claim 8 with said object present is prepared by mathematical analysis of said modification of said radiation beams.

10. A system of a modified Fresnel bi-prism arrangement, having a linear array of small radiation origins, such that the origins are coherent, and two radiation diverging optics, comprising two compound refractive x-ray prisms, such system forming multiple virtual secondary origins of radiation and interference fringes resulting in the portions of multiple overlapped radiation beams, wherein such modulated intensity field progresses longitudinally from the first intersection of overlapped beams, localized in the longitudinal axis in regions of highly visible fringes at certain distances where the laterally displaced fringe patterns superpose resonantly.

11. A system for forming an image of an object, said image including internal features of said object, said system comprising the system of claim 10 with an object in said radiation beams: said image including at least one of phase and scattering content of said object's internal features in a direction along the linear alignment axis of said beam origins.

12. The system of claim 11 wherein said object and said radiation imaging optic are arranged close-coupled to form a compound object/optic for transmitting and modifying said radiation beams.

13. A system of image preparation and display, whereby an image obtained according to the system of claim 12 with said object present is prepared by mathematical analysis of said modification of said radiation beams.

* * * * *